(12) United States Patent
Oliver et al.

(10) Patent No.: US 6,607,512 B2
(45) Date of Patent: Aug. 19, 2003

(54) DEVICE FOR DELIVERY OF LIQUID AND GEL-LIKE SURGICAL MATERIALS AND METHODS FOR USE THEREOF

(75) Inventors: Dana A. Oliver, Plymouth, MA (US); Lawrence F. Travers, Westport, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/757,278

(22) Filed: Jan. 9, 2001

(65) Prior Publication Data

US 2003/0078912 A1 Apr. 24, 2003

(51) Int. Cl.$^7$ ................................ A61K 31/00
(52) U.S. Cl. ................ 604/209; 604/181; 604/187; 604/191; 604/223; 604/224; 604/232
(58) Field of Search ............... 604/181, 187, 604/191, 207–209, 223, 224, 232

(56) References Cited

U.S. PATENT DOCUMENTS

| | | | |
|---|---|---|---|
| 1,250,965 A | 12/1917 | Capwell | |
| 2,491,978 A | * 12/1949 | Helfman et al. | 604/181 |
| 2,750,943 A | 6/1956 | Dann | |
| 2,942,603 A | * 6/1960 | Geyer | 604/224 |
| 3,051,172 A | 8/1962 | Bruchhaus | |
| 3,797,492 A | * 3/1974 | Place | 604/890.1 |
| 4,373,560 A | * 2/1983 | Elsworth | 141/129 |
| 4,472,141 A | 9/1984 | Dragan | |
| 4,682,950 A | 7/1987 | Dragan | 433/90 |
| 4,758,233 A | * 7/1988 | Phillips et al. | 604/232 |
| 4,768,954 A | 9/1988 | Dragan | 433/90 |
| 4,820,287 A | 4/1989 | Leonard | 604/209 |
| 4,946,685 A | * 8/1990 | Edgren et al. | 549/241 |
| 5,000,361 A | 3/1991 | Briddel et al. | 222/575 |
| 5,304,187 A | 4/1994 | Green et al. | 606/151 |
| 5,336,170 A | 8/1994 | Salerno et al. | 604/24 |
| 5,350,387 A | 9/1994 | Semm | 606/151 |
| 5,445,620 A | * 8/1995 | Haber et al. | 604/232 |
| 5,503,623 A | 4/1996 | Tilton, Jr. | 604/13 |
| 5,685,853 A | 11/1997 | Bonnet | 604/164 |
| 5,698,189 A | 12/1997 | Rowe et al. | 424/78.08 |
| 5,715,723 A | 2/1998 | Owens | 72/402 |
| 5,749,968 A | 5/1998 | Melanson et al. | 118/300 |
| 5,766,157 A | 6/1998 | Tilton, Jr. | 604/264 |
| 5,792,099 A | * 8/1998 | DeCamp et al. | 604/506 |
| 5,797,899 A | 8/1998 | Tilton, Jr. | 606/1 |
| 5,906,997 A | 5/1999 | Schwartz et al. | 514/781 |
| 5,964,736 A | * 10/1999 | Lane | 604/207 |
| 6,047,861 A | 4/2000 | Vidal et al. | |
| 6,056,728 A | * 5/2000 | von Schuckmann | 604/207 |

FOREIGN PATENT DOCUMENTS

| | | |
|---|---|---|
| GB | 860997 | 2/1961 |
| WO | WO 99/17834 | 4/1999 |
| WO | WO 99/30629 | 6/1999 |

* cited by examiner

Primary Examiner—J. Casimer Jacyna
(74) Attorney, Agent, or Firm—Richard D. Allison; Thomas J. DesRosier

(57) ABSTRACT

The present invention provides a novel apparatus for delivering a liquid or gel-like surgical material to a target site within a body cavity. The apparatus is characterized in part by an elongated structural member adapted for engagement with a conventional syringe and cannula assembly. In preferred embodiments of the present invention, devices of the invention further comprise a highly flexible applicator tip which permits application of the surgical material at variable delivery angles and even against gravity. Methods also are disclosed for applying the surgical material to the target site using. devices of the present invention.

37 Claims, 8 Drawing Sheets

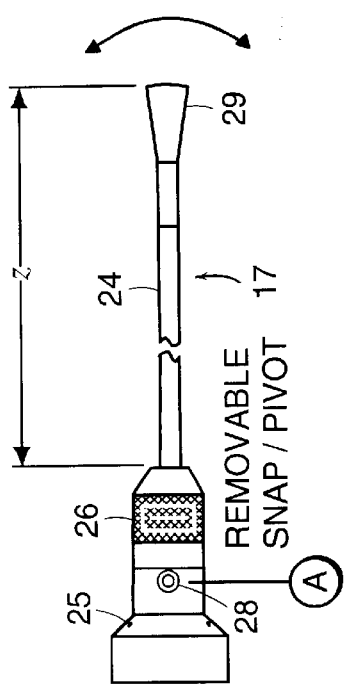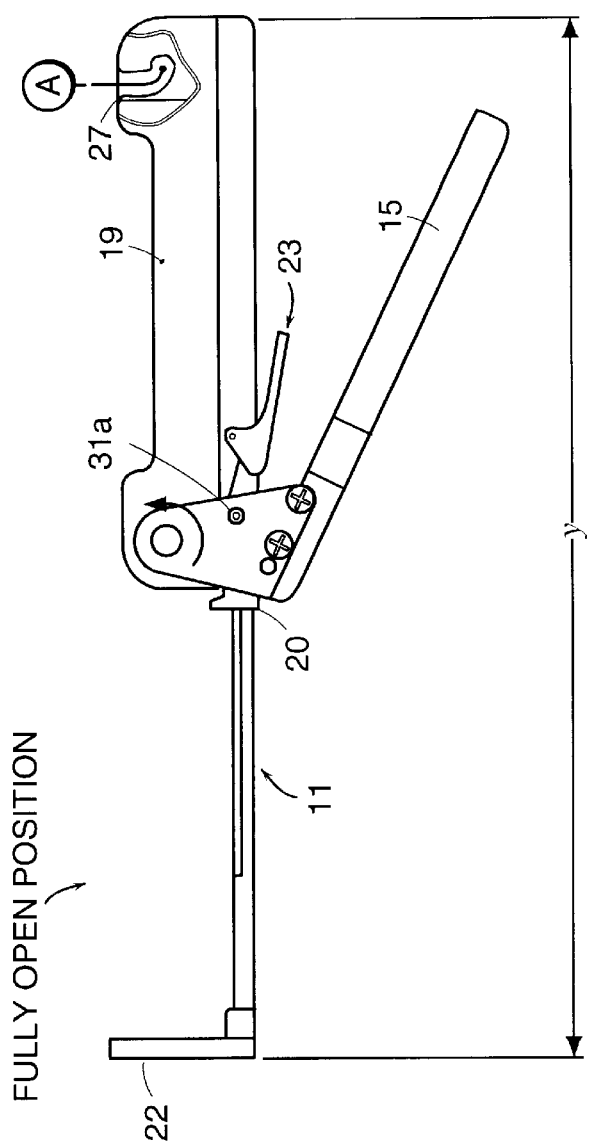

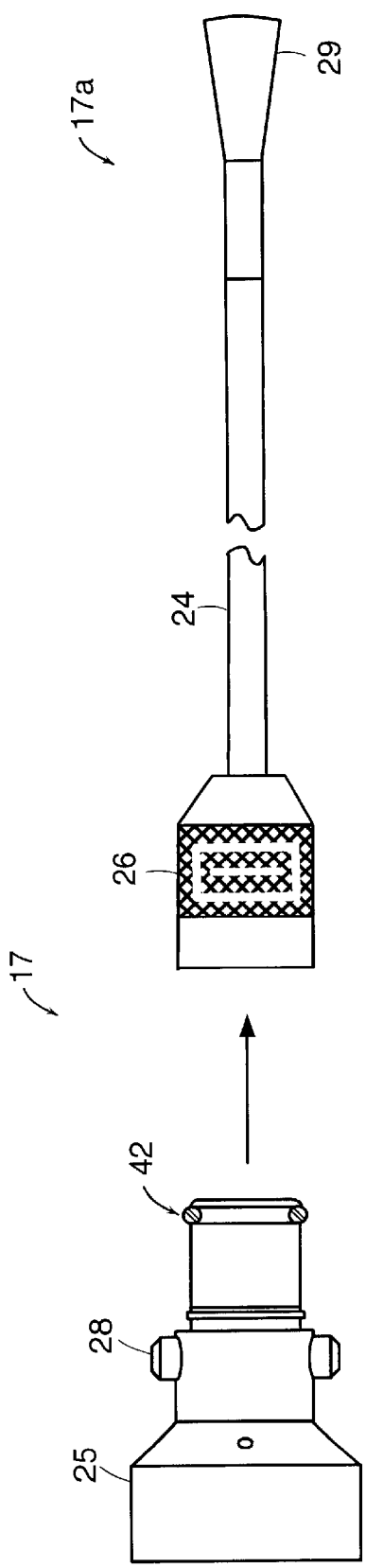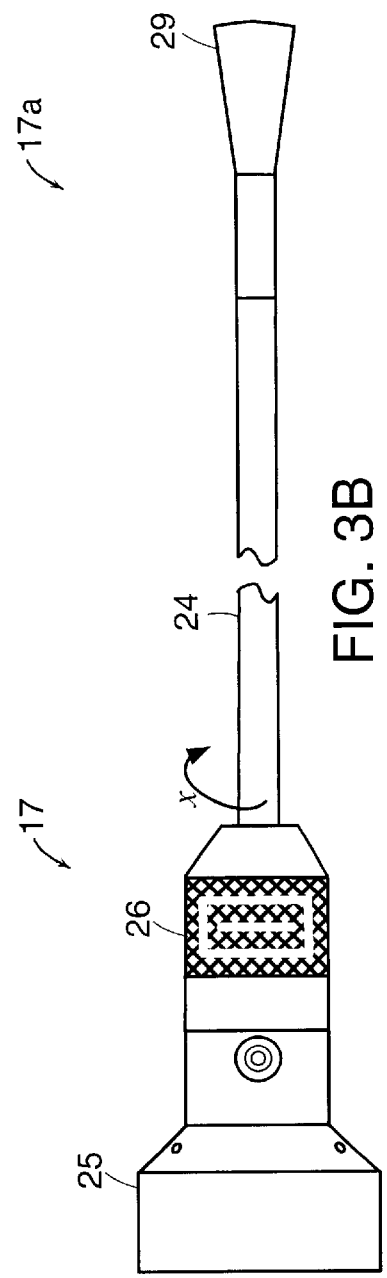
FIG. 3A
FIG. 3B

DEVICE FOR DELIVERY OF LIQUID AND GEL-LIKE SURGICAL MATERIALS AND METHODS FOR USE THEREOF

BACKGROUND OF THE INVENTION

1. Field of the Invention

The present invention relates to a device and method for application of a liquid or gel-like surgical material to a target site within a body cavity. The apparatus and methods of the present invention are suitable for use in laparoscopic and endoscopic surgical procedures, as well as open-incision type procedures.

2. Background

Surgical prosthetic materials are used with a wide variety of surgical procedures. For example, prosthetic materials often are associated with hernia repair. Hernias are abnormal protrusions of an organ or other body structure through a defect or natural opening in a covering membrane, muscle or bone. Hernia repair typically involves replacement of the protruding tissue and repair or reconfiguration of the opening from which it protruded.

Surgical prostheses used in hernia repair and other procedures may include mesh-or gauze-like materials, which support the repaired hernia or other body structures, and/or anti-adhesion barriers, which often are placed between organs or tissues having different structures. Anti-adhesion barriers are used to reduce the incidence and severity of adhesions, e.g., fibrous scar tissue caused by inflammation, which are byproducts of almost all surgical procedures. Such adhesions can cause a variety of highly undesirable post-surgical complications, including small-bowel obstructions, infertility, loss of range of motion and chronic pain. In the case of heart surgery, adhesions are particularly elevate the risk associated with such procedures.

Anti-adhesion barrier products may be in the form of sheets, films, liquids or gels, and are known to prevent the formation of adhesions between internal organs and/or the abdominal wall. Proper placement of such surgical prostheses is sometimes difficult, particularly where laparoscopic and endoscopic surgical procedures are utilized.

Laparoscopic and endoscopic surgical procedures offer significant advantages relative to conventional surgical procedures, and can often avoid the risks associated with such conventional procedures, e.g., bleeding, infection, and damage to organs, nerves and blood vessels.

In laparoscopic procedures, surgery is performed in the interior of the abdomen through narrow tubes inserted therein. Similarly, in endoscopic procedures, surgery is performed in any hollow cavity of the body through narrow endoscopic tubes inserted through small entrance wounds in the skin.

Since only small diameter incisions are required in laparoscopic and endoscopic procedures, trauma to the body (e.g., to the abdominal wall) is minimized, and the time required for healing and post-operative care is significantly shortened.

A number of devices have been developed for use in laparoscopic, endoscopic and open-incision delivery of surgical materials. Many of these devices are suitable for delivery of surgical material in the form of a sheet, film, mesh or gauze to a target site within a body cavity. (See, e.g., U.S. Pat No. 5,503,623, U.S. Pat. No. 5,350,387, and U.S. Pat. No. 5,304,187.)

Certain other laparoscopic and endoscopic devices were developed for delivery of liquid and gel-like medicinal materials. For example, U.S. Pat. No. 5,766,157 reports an instrument consisting of an elongated body adapted to receive a flexible delivery tube having a nozzle at its distal end. The nozzle of the delivery tube can be flexed to dispense a desired spray pattern into a patient's abdominal cavity. However, due to its design and configuration, the device may only be used with low viscosity liquids. More specifically, the device is not capable of advancing a gel or liquid having a higher viscosity through the applicator tip to a target site. Indeed, the small diameter/dual conduit design of that device presents significant back-pressure even when applying a material having a moderate viscosity. Application is further limited in that the tip of the device is not adapted for spreading the medicinal material onto the target site in order to establish an even layer of the anti-adhesion product or other medicinal product. Further, the distal applicator tips are of a fixed size and thus present a limitation when inserted into a trocar. For example, the trocar must have a width greater than the applicator tip to permit the desired laparoscopic or endoscopic application.

There remains a need for improved devices for laparoscopic and endoscopic delivery of a wide variety of surgical materials, particularly liquid and gel-like surgical materials, to target sites within the body cavity. It would be highly desirable if such devices also were suitable for open-incision procedures as well. Further, it would be highly desirable to develop improved devices for laparoscopic, endoscopic and open incision procedures that would permit targeted delivery and even spreading of liquid and gel-like surgical materials including materials having relatively high viscosities. It would be particularly desirable for such devices to offer other mechanical advantages, e.g., reduced back-pressure during operation, as well as improved movement and flexibility within the body cavity for enhanced application of the surgical material.

SUMMARY OF THE INVENTION

Devices of the present invention are suitable for use in a variety of surgical procedures, including laparoscopic, endoscopic and open incision surgical procedures, for application of liquid and gel-like surgical materials to a target site within a body cavity.

Though devices of the present invention may be used for liquid and gel-like surgical materials having a broad range of viscosities, it is particularly well suited for application of relatively high viscosity materials. As used herein, "high viscosity" refers to a viscosity between about 50,000 and about 90,000 centipoise (cp). Devices of the invention are suitable for delivery of numerous types of surgical materials, including anti-adhesion products such as SEPRAGEL (manufactured by Genzyme Corporation) and anatomical fillers such as tissue and organ sealants.

The novel design of the present invention offers surgical and medical personnel a number of advantages over devices of the prior art, including a simplified design, ease of use, flexibility in delivery, and more controlled and effective spreading of the surgical material at the target site. Indeed, the novel design of the present invention even permits dispensing of the surgical material against gravity.

Devices of the present invention generally comprise an elongated structural member (also referred to herein as a "rack") adapted for engagement with a conventional syringe; a cannula/hub assembly to which a highly flexible applicator tip is attached; a surface, e.g., a saddle portion, for holding the syringe that also permits conduit with the cannula/hub assembly and offers axial support to the cannula during the application procedure; and a drive/pawl mechanism which facilitates unloading of the surgical material from the cannula.

The cannula/hub assembly typically comprises a cannula having an elongated shaft which is connected, e.g., snap-fitted, to a hub portion; and preferably a joint which permits rotation of the shaft relative to the hub. The cannula/hub assembly is typically rotatably and removably connected to an interior portion of the device's saddle, e.g., via a snap/pivot assembly. As will be appreciated by those skilled in the art, the cannula/hub assembly may be constructed of various materials, e.g., stainless steel, rigid epoxies, aluminum and the like.

As noted above, devices of the invention preferably comprise an applicator tip which is attached to the distal end of the cannula. Such a tip is preferably highly flexible, e.g., foldable, cylindrically adaptable and otherwise manipulatable, and permits application of the surgical material at variable delivery angles and against gravity. In particularly preferred embodiments of the invention, the applicator tip has a fan-shaped configuration. By way of illustration, the highly flexible fan-shaped applicator tip essentially allows the surgeon to apply the gel or liquid surgical material as one would apply paint to any given surface with a paint brush. In that way, targeted and controlled application of an even layer of surgical material is achieved.

The drive/pawl mechanism is preferably actuated by a handle or like feature that is easily accessible from a position external to the body cavity. In that way, the surgical material may be dispensed from the leading or distal end of the cannula without removing the apparatus from the body cavity.

Additionally, preferred embodiments of the invention further comprise a secondary mechanism (referred to herein as an "anti-backlash lever") which prevents syringe plunger expansion and permits air bolus priming.

Priming is typically performed before application of the surgical material to the target site, and preferably prior to introduction of the device into the trocar or secondary cannula (if the procedure is a laparoscopic or endoscopic one). Priming ensures that the surgical material, e.g., gel, is in a "ready to dispense" mode and also ensures precision and accuracy with respect to the amount of gel to be delivered. Additionally, priming generally results in a small amount of the gel being applied to the applicator tip which acts as a lubricant and allows for easier transition of the device through the trocar or secondary cannula.

The anti-backlash lever also is critical during changeover of an empty or nearly empty (spent) syringe to a syringe containing an additional volume of surgical material. Upon actuation, the anti-backlash lever disengages the rack of the device so that the syringe may be removed and replaced without disrupting the on-going surgical procedure. Further, during such a changeover, air can become trapped in the cannula between one or more sections of the gel resulting in the presence of a compressible volume of air. Using devices of the present invention, that volume of air can easily be expensed and eliminated by re-priming of the device.

Though generally less preferred, as an alternative to the anti-backlash lever, another type of secondary mechanism may be employed for priming and preventing unwanted syringe plunger expansion. One example of such a mechanism preferably comprises a panel to which a manually operable spring-reinforced assembly is attached. In this embodiment, advancement of the surgical material and priming are achieved by actuation of one or more pivot levers which are in communication with the spring-reinforced assembly.

Using devices of the present invention, the surgical material is initially loaded into the syringe in a conventional manner; the syringe is connected to the cannula/hub assembly, e.g., by a luer taper fit connector, and seated in the saddle portion of the device. The device is preferably then primed by advancing the syringe plunger as needed, e.g., by applying forward pressure to the syringe plunger or using the handle to partially advance the drive/pawl mechanism. Once in proximity of the target site, the pawl/drive mechanism is actuated thereby advancing (unloading) the surgical material through the cannula at its distal end via the highly flexible fan-shaped applicator tip. In that way, devices of the invention permit flexible application of the surgical material to the target site with ease, accuracy and precision.

In addition to entry into the body cavity through an open incision, devices of the invention may be introduced through a conventional trocar during laparoscopic or endoscopic surgical procedures. For facile entry and movement within the trocar during such procedures, the applicator tip may be prolapsed or otherwise folded about the distal end of the cannula.

Methods for delivering a surgical material to a target site using devices of the present invention also are provided.

Methods of the invention generally comprise providing a device in accordance with the present invention, e.g., a device comprising a rack adapted for engagement with a conventional syringe, a cannula/hub assembly to which a suitable applicator tip is attached, a saddle for seating the syringe which permits conduit with the cannula/hub assembly, and a drive/pawl mechanism in communication with the rack for advancing the surgical material through the cannula/hub assembly; loading the surgical material into the syringe; connecting the syringe to the cannula/hub assembly, e.g., via a slip fit or self-locating type of engagement; seating the syringe in the saddle of the device; inserting the cannula portion of the device into the body cavity, e.g., directly or via a conventional trocar; positioning the applicator tip within proximity of the target site; applying the surgical material to the target site; and withdrawing the apparatus from the body cavity.

Preferred methods of the invention also may comprise priming the syringe and/or cannula. Priming may be achieved by forwardly advancing the syringe plunger or by actuation of the drive/pawl mechanism, e.g., using the handle of the device.

Methods of the invention also may further comprise replacing a spent syringe with a syringe containing an additional volume of surgical material during the application procedure. For example, certain procedures may require that a large volume of surgical material be applied to the target site. In such procedures, after the syringe has dispensed all or nearly all of its contents, it may be replaced with another syringe or with the same syringe which has been reloaded with additional surgical material. Using the anti-backlash lever (or the alternate secondary mechanism described above), the changeover of syringes can be achieved without removing the device from the body cavity or otherwise disrupting the procedure. Moreover, using devices of the invention, re-priming can be performed to eliminate air which might otherwise be introduced due to the changeover.

Preferred methods of the present invention also may comprise manipulating the leading or distal end of the cannula to facilitate application of the surgical material at variable delivery angles. Indeed, devices of the invention even permit dispensing of the surgical material against gravity. A highly flexible fan-shaped applicator tip is typically attached, e.g., via insert-molding or adhesive, to the distal end of the cannula to facilitate such manipulation during the application procedure.

The foregoing and other objects, features and advantages of the invention will become better understood with reference to the following description and appended claims.

BRIEF DESCRIPTION OF THE DRAWINGS

FIGS. 2A–2B show a partially disassembled device of the present invention.

FIGS. 3A–3B show a cannula/hub assembly in a preferred embodiment of the present invention (partially-assembled and fully-assembled).

DETAILED DESCRIPTION OF THE INVENTION

As discussed above, devices of the present invention are suitable for use in a variety of surgical procedures, including laparoscopic, endoscopic and open incision surgical procedures, for application of liquid and gel-like surgical materials to a target site within a body cavity. Devices of the invention are well-suited for application of surgical materials having a wide range of viscosities. Indeed, the novel design of the device is non-limiting with respect to the viscosity of the surgical material. Further, devices of the present invention are characterized in part by a highly flexible applicator tip which permits delivery of the surgical material at variable delivery angles. Moreover, the novel design of the present invention even permits dispensing of the surgical material against gravity.

Figure 1:
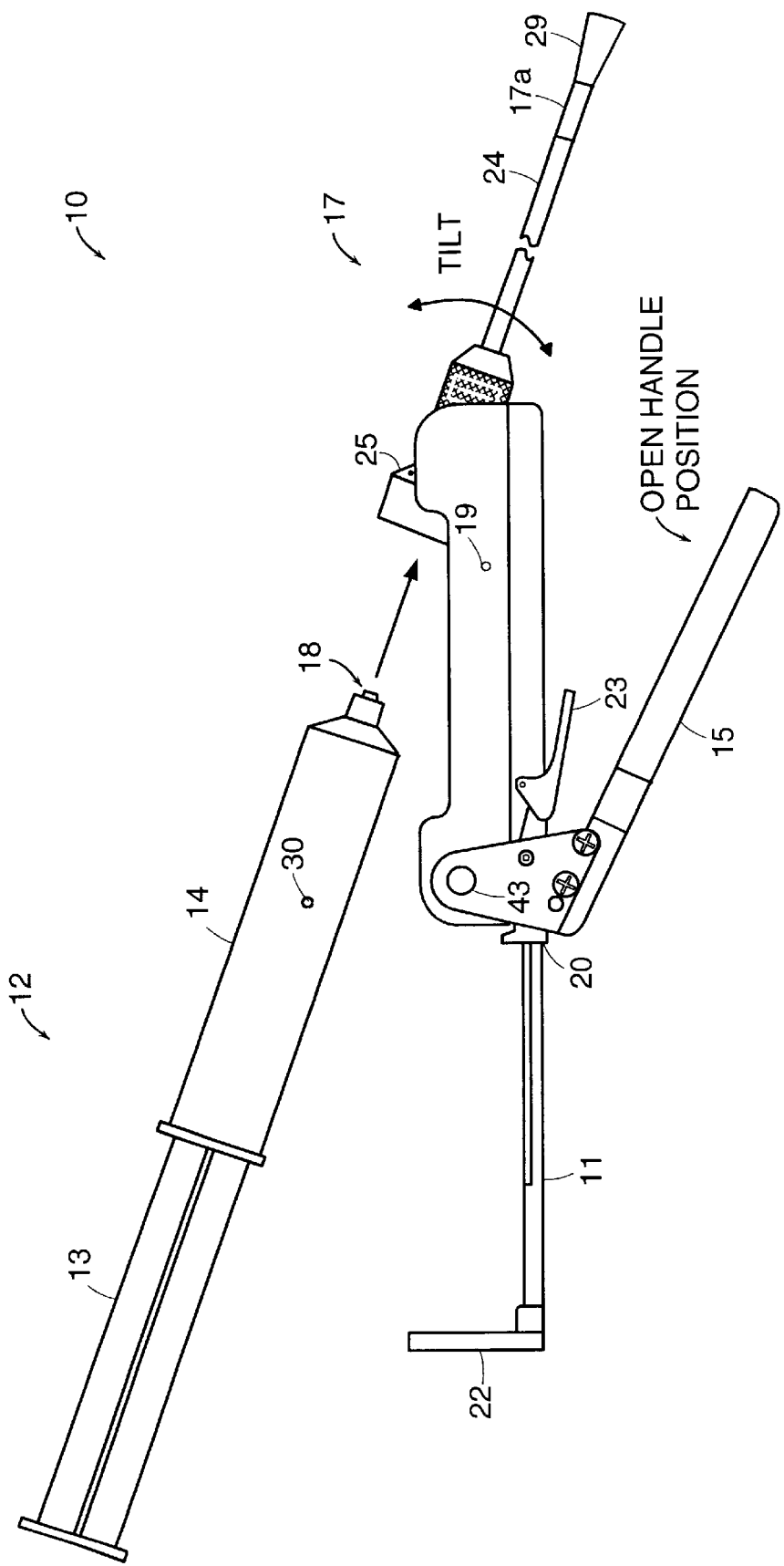
FIG. 1 shows a preferred embodiment of a device of the present invention.

Referring to FIGS. 1 and 2A/B, in a preferred embodiment of the present invention, device 10 is shown to include an elongated structural member 11 (also referred to herein as a "rack") adapted for engagement with a conventional syringe 12 having a plunger 13 and syringe craddle/body 14. Syringe 12 is preferably removably connected, e.g., by a luer slip lock connector 18, to a cannula/hub assembly 17. As shown in FIG. 1, syringe 12 is loaded with a desired surgical material 30.

Devices of the invention further comprise a flexible applicator tip 29 which preferably has a fan-shaped configuration and is attached to cannula/hub assembly 17 at its distal end 17a. (In accordance with conventional practice regarding medical devices, "proximal end" designates that end which is closest to the medical personnel manipulating the device, and "distal end" designates the opposite end that is placed within a patient.).

Figure 5:
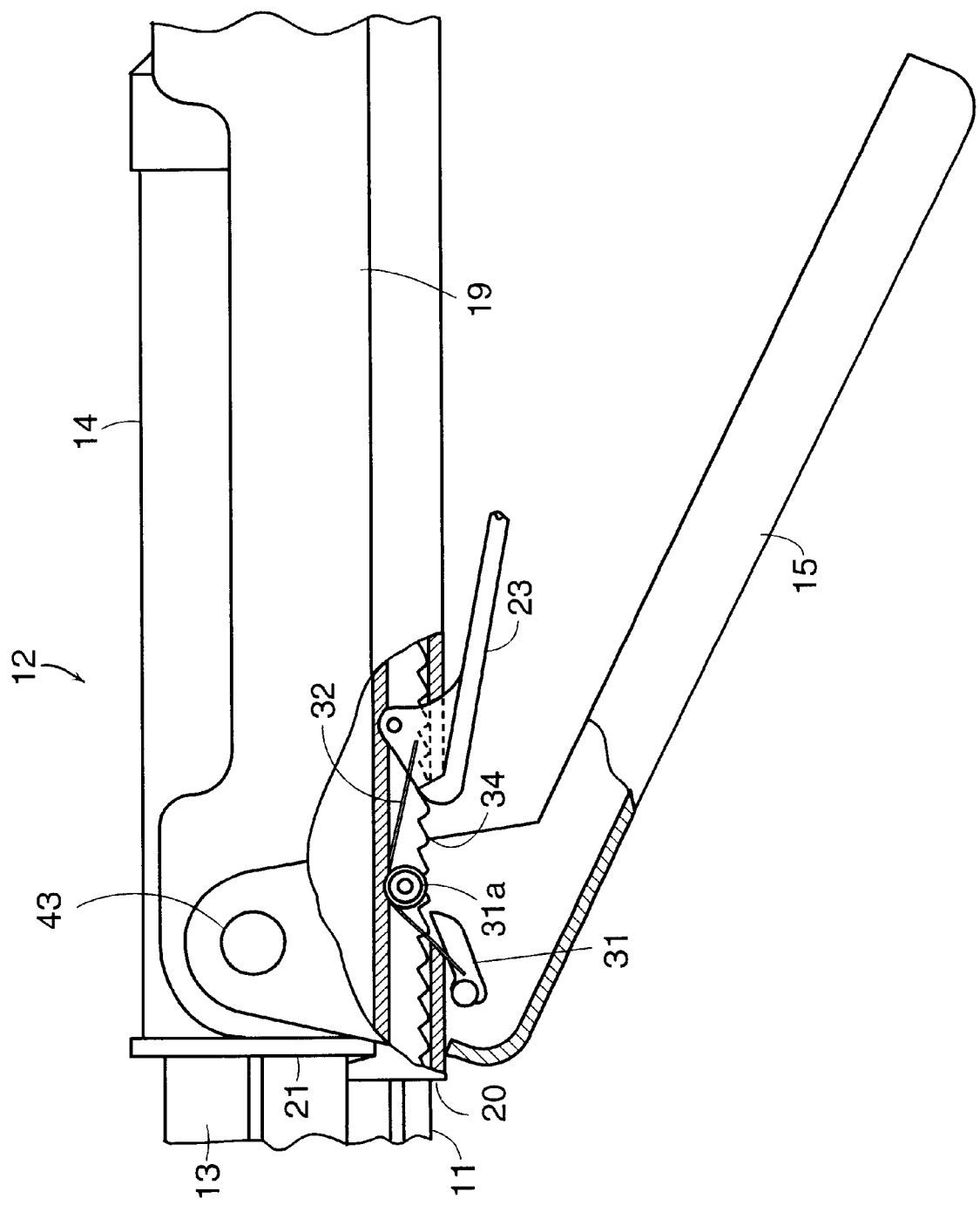
FIG. 5 is a partial cross-sectional view of the handle and drive/pawl mechanism of the device of FIG. 4 where the handle is in an open position (non-advanced pawl position).
Figure 6:
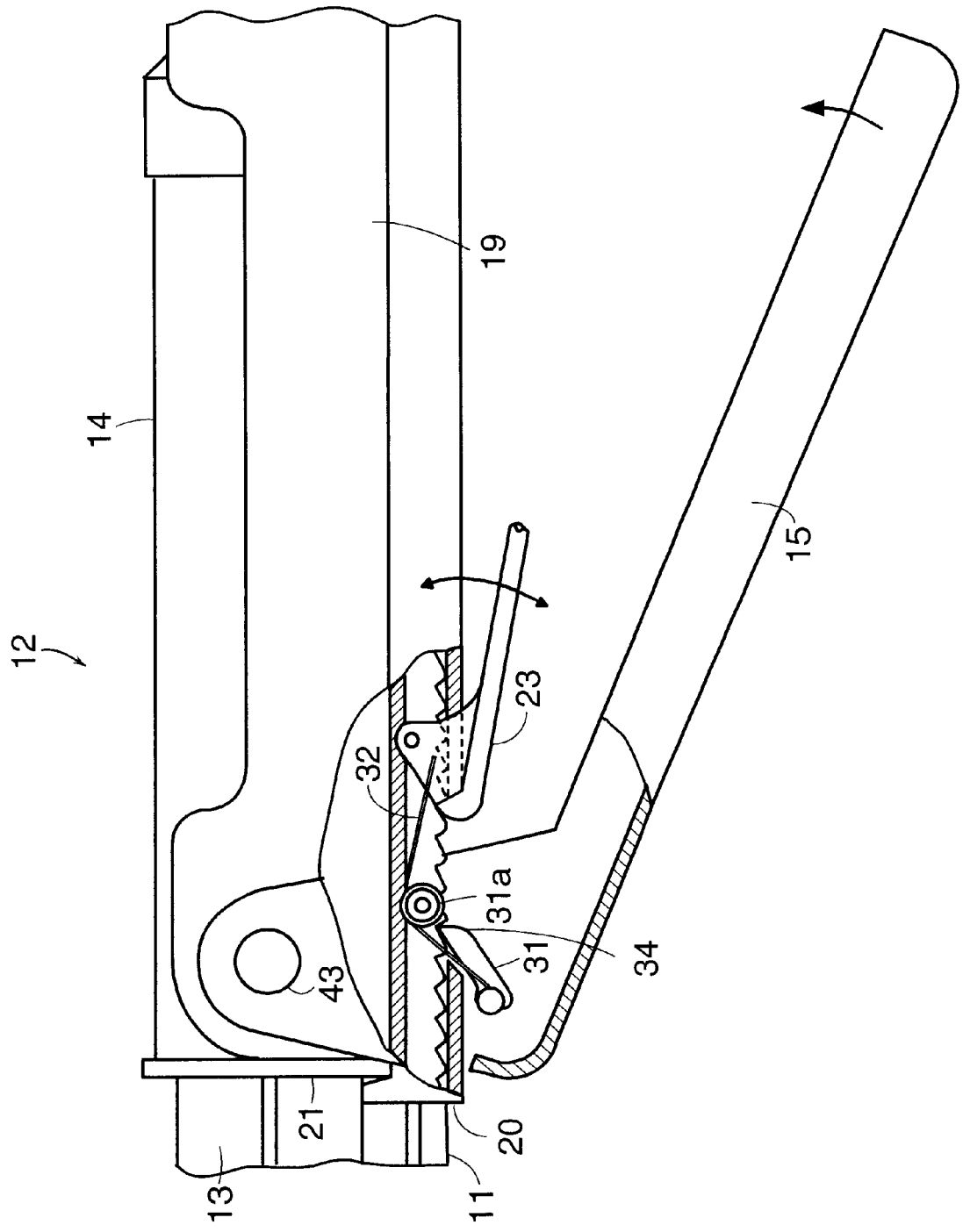
FIG. 6 is a partial cross-sectional view of the handle and drive/pawl mechanism of the device of FIG. 4 where the handle is in a partially advanced position.
Figure 7:
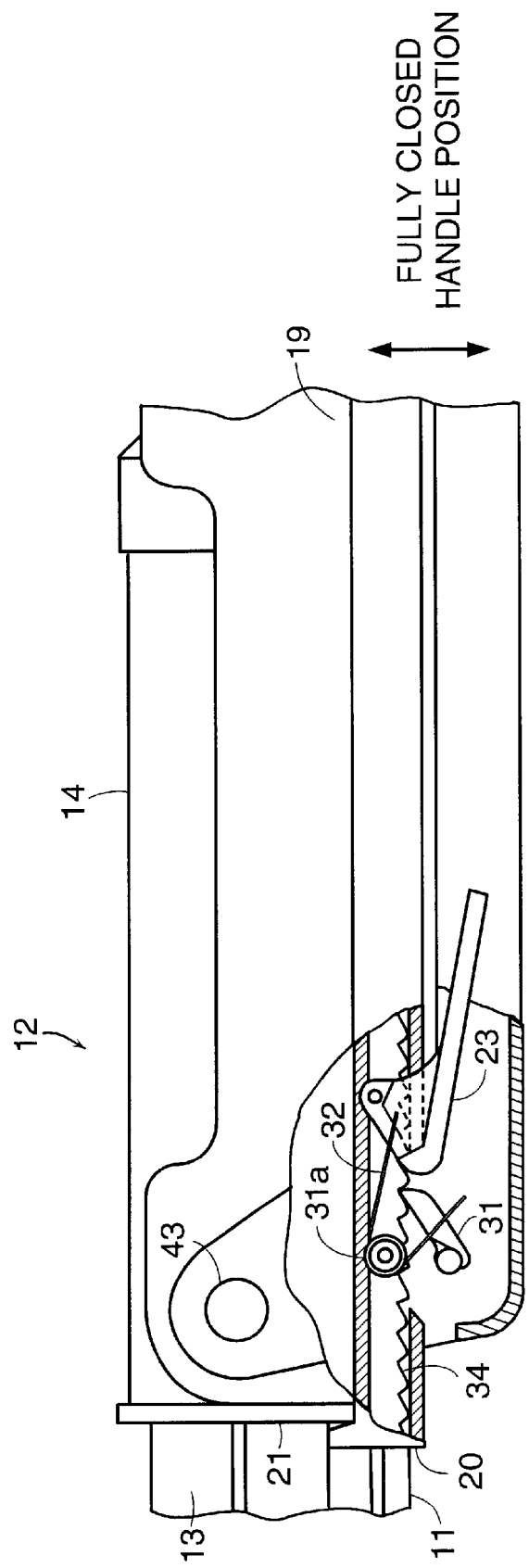
FIG. 7 is a partial cross-sectional view of the handle and drive/pawl mechanism of the device of FIG. 4 where the handle is in a closed position (fully-advanced pawl position).

Referring also to FIGS. 5, 6 and 7, a handle 15 in communication with a drive/pawl mechanism 31 facilitates unloading of the surgical material from the device once in proximity of the target site. Handle 15 is preferably easily accessible from a position external to the body cavity. In that way, surgical material may be dispensed from the leading or distal end of the cannula 17a without removing the device from the body cavity. Handle 15 preferably communicates with saddle portion 19 of the device via one or more handle pivot points 43 located on either side of the saddle (See, e.g., FIGS. 1, 5, 6 and 7). Handle 15 and drive/pawl mechanism 31 permit precise, ratchet-like advancement of the surgical material.

Device 10 preferably also comprises a surface, e.g., saddle 19, on which syringe 12 is seated and which permits conduit with cannula/hub assembly 17. Saddle portion 19 also provides axial support to the cannula/hub assembly 17 during the application procedure. Referring with particularity to FIGS. 2A/B and 4, device 10 further comprises a syringe plunger tail stop 22, and a locking lip 20 which facilitates locating of syringe 12 into the device and which secures flange 21 of syringe 12.

Cannula/hub assembly 17 connects to syringe 12 and facilitates dispensing of the surgical material at the desired target site. Referring now to FIGS. 2A/B and 3A/B, preferably cannula/hub assembly 17 comprises a cannula having an elongated shaft 24 which is connected, e.g., snap-fitted, to hub 25 via knurl 26 and other conventional means, e.g., one or more O-rings 42. In particularly preferred embodiments of the invention, shaft 24 is recessed, e.g., tapered or slightly narrower in diameter, at its distal end to accommodate applicator tip 29, particularly in a prolapsed form. Such a prolapsed form facilitates easy insertion and traversal of the device through a conventional trocar during a laparoscopic or endoscopic procedure. Preferably, knurl 26 contains a joint (not shown) which permits rotation of the shaft (denoted by x in FIG. 3B) relative to the hub portion 25. The cannula/hub assembly 17 is typically rotatably and removably connected to the saddle portion 19 of the device 10, e.g., via a snap/pivot assembly 27, 28 (as shown in FIGS. 2A/2B).

Referring again to FIGS. 1 and 2A/B, in preferred embodiments of the present invention, device 10 also comprises a secondary mechanism, lever 23 (referred to herein as an "anti-backlash lever") which communicates with drive/pawl mechanism 31 via pawl 31a. Lever 23 prevents syringe plunger expansion and permits air bolus priming of syringe 12 once the syringe is seated in saddle portion 19 or otherwise engaged by rack 11. Using devices of the invention, priming may be achieved quite easily, e.g., the syringe plunger 13 may be advanced as necessary to expense air from syringe 12 and/or cannula/hub assembly 17.

Priming is typically performed before application of the surgical material to the target site. In the case of laparoscopic and endoscopic procedures, priming is preferably performed prior to introduction of the device into the trocar or secondary cannula. Priming ensures that the surgical material is in a "ready to dispense" mode and also ensures precision and accuracy with respect to the amount of gel to be delivered. Additionally, priming generally results in a small amount of the surgical material being advanced into the applicator tip. In that way, priming adds a lubricant to the applicator tip and generally facilitates an easier transition of the device through the trocar or secondary cannula.

The anti-backlash lever 23 also is a particularly important feature during changeover of an empty or nearly empty (spent) syringe to a syringe containing an additional volume of surgical material. Upon actuation, the anti-backlash lever disengages rack 11 of the device so that syringe 12 may be removed and replaced without disrupting the on-going procedure. More specifically, with anti-backlash lever 23 depressed, rack 11 is disengaged and the plunger backstop may be moved in a rearward motion such that the syringe 12 can be removed from device 10. Once reloaded, syringe 12 may be reinserted into device 10, and the device re-primed as needed.

Figure 8:
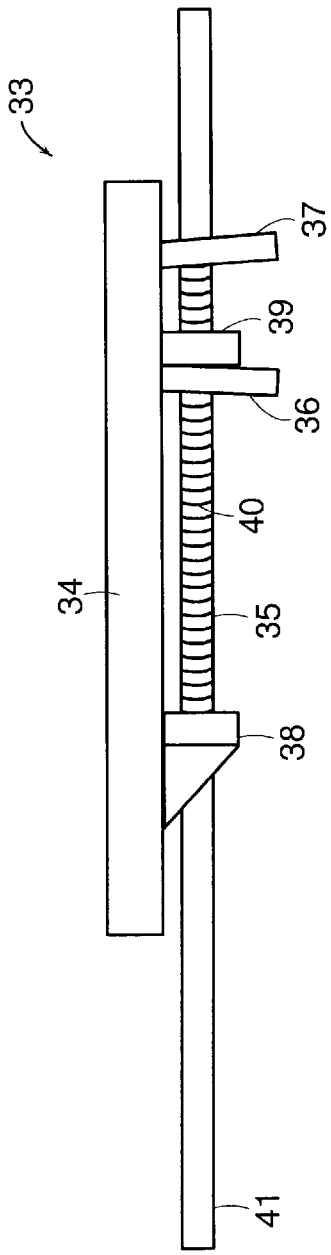
FIG. 8 shows an alternate secondary mechanism for priming a device of the present invention.

Additionally, though generally less preferred, as an alternative to the anti-backlash lever, another type of secondary mechanism may be employed which is adapted for communication with the rack of the device and which is useful for priming and preventing syringe plunger expansion. FIG. 8 illustrates one example of such a mechanism. As shown, alternate priming mechanism 33 preferably comprises a panel 34 to which a manually operable spring-reinforced assembly 35 is attached via sub-panels 38, 39. In this embodiment, priming is achieved by actuation of one or more levers 36, 37 in communication with the spring-reinforced assembly 35 to eliminate air from the syringe and/or cannula/hub assembly. Spring-reinforced assembly 35 comprises a cylindrical rod 41, preferably constructed of stainless steel or the like, which extends through sub-panels 38, 39 and about which a flat or rounded stainless steel wire, e.g., denoted by coil 40, is fitted. In this embodiment, a handle or like feature (e.g., comparable to handle 15 in FIG. 1) would communicate with pivot lever 37 to apply forward movement to cylindrical rod 41. In that way, the function of rod 41 is analogous to that of the rack 11 and rack teeth 34, and pivot levers 36,37 replace drive/pawl mechanism 31.

As noted above, fan-shaped applicator tip 29 is attached to cannula/hub assembly 17 at its distal end 17a. Applicator tip 29 is preferably highly flexible, e.g., foldable and cylindrically adaptable or otherwise manipulatable, to permit application of the surgical material at variable delivery angles and against gravity. Preferably, applicator tip 29 is made of urethane or other suitable, non-reactive, flexible materials, e.g., polyvinylcarbonate (PVC), ethylene and the like. It also is generally preferred that the applicator tip material be made from a transparent/translucent plastic. For use in accordance with devices of the invention, polyurethane, USP Class VI, Shore "A" having a durometer rating of 50–70 is a particularly preferred applicator tip material, in part, for its optimal stiffness and memory.

Figure 9B:
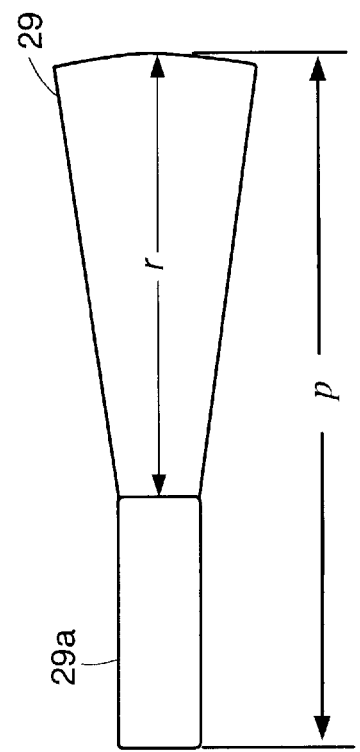
FIGS. 9A–9C show the applicator tip of the device in a preferred embodiment of the present invention.
Figure 9C:
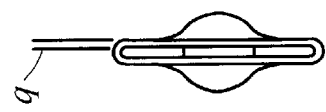
Figure 9A:
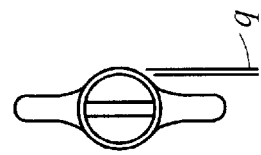

Referring now also to FIGS. 9A/B/C, a preferred applicator tip 29 is shown in further detail. A relatively narrow portion 29a of applicator tip 29 is suitable for attachment to the distal end of stainless steel shaft 24. Preferred dimensions for applicator tip 29 will vary widely as will be appreciated by those skilled in the art. In certain preferred embodiments, applicator tip 29 has dimensions of about 1.0 to about 2.0 inches in overall length, more preferably about 1.5 inches in length (distance p in FIG. 9A); a wall thickness of about 0.010 to about 0.025 inches in diameter, more preferably about 0.015 to about 0.020 inches in diameter (distance q in FIGS. 9A/C). The fan portion of applicator tip 29 is preferably about 0.5 to 1.5 inches in length (distance r in FIG. 9B). Other dimensions, including longer applicator tips, also will be suitable.

Using devices of the present invention, the surgical material 30 is initially loaded into the syringe in a conventional manner; the syringe 12 is connected to the cannula/hub assembly 17, e.g., by luer taper slip-fit connector 18, and seated in the saddle 19 of device 10; the syringe is then primed. Once in proximity of the target site, the pawl/drive mechanism 31 is actuated, e.g., by handle 15 or other like feature, thereby advancing (unloading) surgical material 30 through the cannula/hub assembly 17 at its distal end 17a via the applicator tip 29. In that way, a wide variety of liquid and gel-like surgical materials can be flexibly applied with ease, accuracy and precision. Further, delivery of the surgical material is visually confirmed as the liquid or gel can be seen through the translucent material of the applicator tip 29.

As noted above, drive/pawl mechanism 31 facilitates unloading of the surgical material from the cannula/hub assembly 17. Referring with particularity to FIGS. 4, 5, 6 and 7, the drive/pawl mechanism 31 is actuated by handle 15, e.g., by depressing the handle to a desired angle. Angular protrusions (referred to as "rack teeth") 34 positioned longitudinally along the interior of rack 11 engage and secure drive/pawl mechanism 31 once the desired degree of advancement/actuation is achieved and the desired volume of surgical material has been dispensed.

In a typical operation, the drive/pawl mechanism 31 positively engages into one of the rack teeth 34 and remains engaged until either the handle 15 is fully depressed or fully released. The anti-backlash lever 23 is positively engaged by the aid of one or more torsion springs 32 into each rack tooth as it passes by the anti-backlash lever 23 and only disengages by manually depressing the lever 23. Further, devices of the invention may be configured such that each handle actuation precisely advances the syringe to dispense a specific volume of surgical material. For example, in particularly preferred embodiments of the invention, one handle actuation dispenses about 4–5 cc of liquid or gel. However, devices of the invention are readily adaptable to different actuation/volume configurations.

Figure 4:
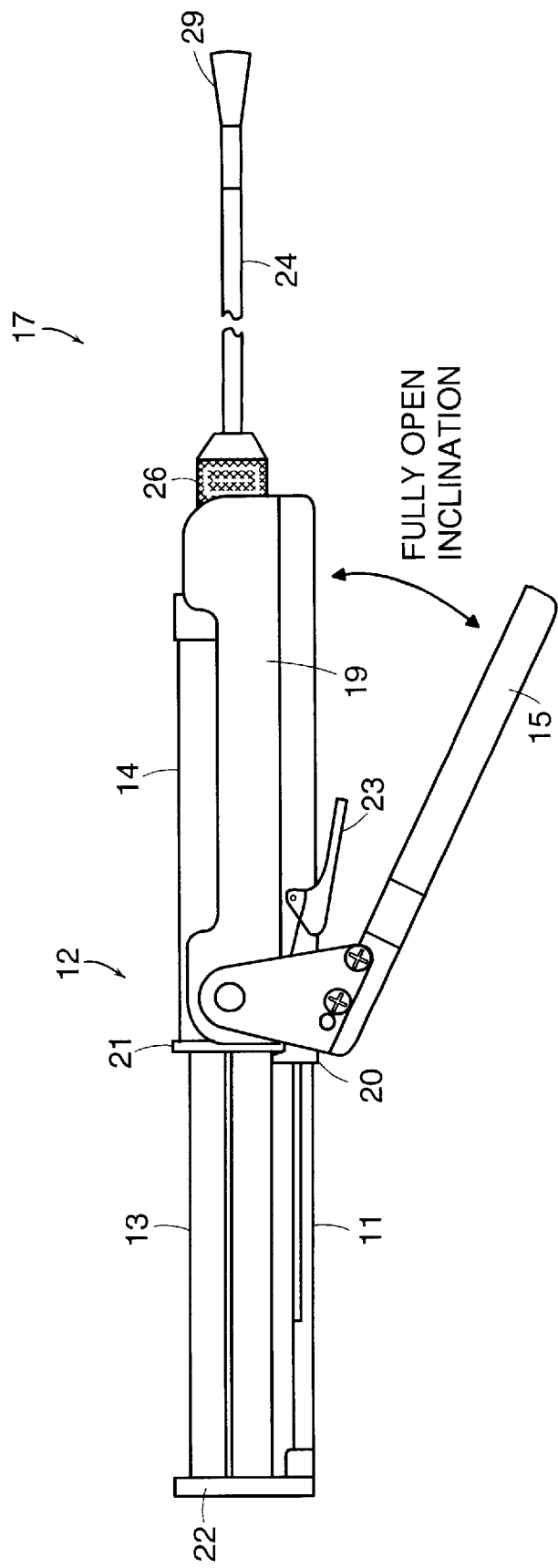
FIG. 4 shows the device of FIG. 1 loaded and prepared for delivery of a desired surgical material.

Referring with particularity to FIGS. 4 and 5, handle 15 is shown in an open position and the drive/pawl mechanism is not advanced. Alternately, FIG. 6 shows handle 15 in a partially closed position; and FIG. 7 shows the handle in a fully closed position with the drive/pawl mechanism in a fully advanced position.

Preferably, handle 15 of device 10 is easily accessible from a position external to the body cavity. In that way, the surgical material 30 may be dispensed from the cannula 17 at its leading or distal end 17a without removing the device from the body cavity.

Suitable dimensions of the components of devices of the present invention can vary rather widely depending on the intended application and such dimensions can be readily determined by those skilled in the art based on the present disclosure.

For example, dimensions for device 10 (e.g., end to end, including rack 11 and saddle 19) and cannula 24 are shown in FIGS. 2A/B, respectively as y and z. Generally preferred dimensions for device 10 include a length of about 8 to about 12 inches, more preferably about 10 to about 12 inches, most preferably about 11.5 inches. Generally preferred dimensions for cannula portion 24 include a length of about 8 to about 15 inches, more preferably about 10 to about 14 inches, most preferably about 12.5 inches.

In the event that the device is being used in an open incision procedure, a device having a relatively shorter cannula/hub assembly may be desirable, as will be appreciated by the skilled artisan. Additionally, the syringe and cannula/hub assembly could be used in open incision procedures alone, e.g., without engagement to the remaining portions of the device. In that way, application of the surgical material could be achieved without use of the rack, saddle and pawl/drive mechanism of the device.

In addition to entry into the body cavity via an open incision, devices of the invention may be introduced through a conventional trocar during laparoscopic or endoscopic surgical procedures.

Methods for delivering a surgical material to a target site using devices of the present invention also are provided.

Methods of the invention generally comprise providing a device in accordance with the present invention, e.g., a device comprising a rack adapted for engagement with a conventional syringe, a cannula/hub assembly to which a suitable applicator tip is attached, a saddle for seating the syringe which permits conduit with the cannula/hub assembly, and a drive/pawl mechanism in communication with the rack for advancing the surgical material through the cannula/hub assembly; loading the surgical material into the syringe; connecting the syringe to the cannula/hub assembly, e.g., via a slip fit or self-locating type of engagement; seating the syringe in the saddle of the device; inserting the cannula portion of the device into the body cavity, e.g., directly or via a conventional trocar; positioning the applicator tip within proximity of the target site; applying the surgical material to the target site; and withdrawing the apparatus from the body cavity.

Preferred methods of the invention also may comprise priming the syringe and/or cannula using a secondary mechanism, e.g., the anti-backlash lever or alternative priming mechanism described above. Such a mechanism prevents syringe plunger expansion and permits forward advancement of the syringe to expense and eliminate unwanted air.

Methods of the invention also may further comprise replacing a spent syringe with a syringe containing an additional volume of surgical material during the application procedure. For example, certain procedures may require that a large volume of surgical material be applied to the target site. In such procedures, after the syringe has dispensed all or nearly all of its contents, it may be replaced with another syringe or with the same syringe which has been reloaded with additional surgical material. Using devices of the invention, the changeover of syringes can be achieved without removing the device from the body cavity or otherwise disrupting the procedure. Upon actuation, the anti-backlash lever disengages the rack of the device for easy removal and replacement of the syringe. Re-priming of the device can then be performed to expense and eliminate air which might otherwise be introduced due to the changeover.

Preferred methods of the present invention also may comprise manipulating the leading or distal end of the cannula to facilitate application of the surgical material at variable delivery angles and, if necessary, against gravity. A highly flexible fan-shaped applicator tip is typically attached, e.g., via insert-molding or adhesive, to the distal end of the cannula to facilitate such manipulation during the application procedure.

Methods of the invention are further illustrated by the schematic presentation set forth below.

| SCHEMATIC 1 | |
|---|---|
| Step 1: | Prepare the delivery device (fully extend the structural member/rack of the device). |
| Step 2: | Snap the cannula/hub assembly into the structural member/rack of the device. |
| Step 3: | Insert the syringe loaded with the desired surgical material into the cannula/hub assembly. |
| Step 4: | Snap the loaded syringe into the saddle of the device. |
| Step 5: | Prime the device as necessary, e.g., by depressing the handle until the surgical material exits the cannula at its distal end. |
| Step 6: | Approximate the distal end of the cannula to the desired anatomical field, e.g., bodily structure or tissue. |
| Step 7: | Locate and position the applicator tip at the target anatomical site. |
| Step 8: | Apply the surgical material as desired, e.g., by depressing the device's handle, to administer the desired volume of surgical material to the target anatomical site. |
| Step 9: | Spread the surgical material as desired at the target anatomical site. |
| Step 10: | Repeat the procedure as necessary at the same or an alternate anatomical site. |

Referring to the steps outlined above, it is noted that the devices and methods of the invention may be used for a variety of surgical procedures. Particularly preferred surgical materials for use in connection with the devices and methods of the invention, include adhesion barrier materials (e.g., used to prevent adhesions following surgical procedures), and anatomical fillers and sealant materials (e.g., used for sealing bodily tissues and organs in cardiovascular and cardiothoracic procedures). Particular bodily tissues targeted for application of such materials include cardiac tissue and abdominal tissue.

The terms and expressions which have been employed herein are used as terms of description and not of limitation. There is no intent, in the use of such terms and expressions, of excluding any of the equivalents of the features shown and described or portions thereof, but it is recognized that various modifications are possible within the scope of the invention claimed.

What is claimed is:

1. A device for delivery of a liquid or gel-like surgical material into a body cavity comprising:
   a) an elongated structural member adapted for engagement with a conventional syringe;
   b) a cannula assembly capable of engagement with the syringe;
   c) a saddle portion in which the syringe is seated and which permits flow communication of the surgical material through the cannula assembly; and
   d) a drive mechanism in communication with the elongated structural member for advancing the surgical material through the cannula assembly wherein the surgical material has a viscosity greater than about 50,000 centipoise.

2. The device of claim 1 wherein the syringe is removably connected to the cannula assembly.

3. The device of claim 1 wherein the cannula assembly is rotatably connected to the saddle.

4. The device of claim 1 wherein the cannula assembly is removably connected to the saddle.

5. The device of claim 1 wherein the cannula assembly is connected to the saddle via a pivot assembly.

6. The device of claim 1 wherein the drive mechanism is actuated by a handle thereby advancing the surgical material through the cannula assembly.

7. The device of claim 6 wherein the handle is accessible from a position external to the body cavity during delivery of the surgical material.

8. The device of claim 1 further comprising a secondary mechanism which disengages the elongated structural member upon actuation.

9. The device of claim 1 further comprising a secondary mechanism which prevents syringe plunger expansion and permits air bolus priming.

10. The device of claim 1 further comprising an applicator tip attached to the cannula assembly at its distal end.

11. The device of claim 10 wherein the applicator tip comprises a flexible material.

12. The device of claim 11 wherein the flexible material is shaped as a collapsible fan shaped member.

13. The device of claim 10 wherein the applicator tip has a fan-shaped distal end.

14. The device of claim 1 wherein the surgical material is an anti-adhesion barrier having a viscosity between about 50,000 to 90,000 centipoise.

15. A device for delivery of a liquid or gel-like surgical material into a body cavity comprising:
   a) an elongated structural member adapted for engagement with a conventional syringe;
   b) a cannula assembly capable of engagement with the syringe;
   c) a saddle portion in which the syringe is seated and which permits flow communication of the surgical material through the cannula assembly;
   d) a drive mechanism in communication with the elongated structural member for advancing the surgical material through the cannula assembly;
   e) an applicator tip attached to a distal end of the cannula assembly; and
   f) a secondary mechanism for air bolus priming of the syringe wherein the secondary mechanism disengages the elongated structural member upon actuation.

16. The device of claim 15 wherein the drive mechanism is advanced by actuation of a handle in communication therewith.

17. The device of claim 15 wherein the syringe is removably seated in the saddle.

18. The device of claim 15 wherein the applicator tip has a fan-shaped distal end.

19. A device for delivery of a liquid or gel-like surgical material into a body cavity comprising:
   a) an elongated structural member adapted for engagement with a conventional syringe;
   b) a cannula assembly capable of engagement with the syringe;
   c) a saddle portion in which the syringe is seated and which permits flow communication of the surgical material through the cannula assembly;
   d) one or more pivot levers in communication with the elongated structural member for advancing the surgical material through the cannula assembly;
   e) an applicator tip attached to a distal end of the cannula assembly; and
   f) a secondary mechanism for air bolus priming of the syringe wherein the secondary mechanism disengages the elongated structural member upon actuation.

20. The device of claim 19 wherein the elongated structural member communicates with a spring-reinforced assembly to prevent syringe plunger expansion and permit air bolus priming.

21. A device for delivery of a liquid or gel-like surgical material into a body cavity comprising:
   a) an elongated structural member adapted for engagement with a conventional syringe;
   b) a cannula assembly capable of engagement with the syringe;
   c) a saddle portion in which the syringe is seated and which permits flow communication of the surgical material through the cannula assembly;
   d) one or more pivot levers in communication with the elongated structural member for advancing the surgical material through the cannula assembly;
   e) an applicator tip attached to a distal end of the cannula assembly; and
   f) a secondary mechanism for air bolus priming of the syringe wherein the secondary mechanism disengages the elongated structural member upon actuation and wherein the elongated structural member communicates with a spring-reinforced assembly to prevent syringe plunger expansion and permit air bolus priming and wherein the spring-reinforced assembly comprises a cylindrical rod about which a flat or rounded coil is fitted.

22. A method of delivering a surgical material to a target site within a body cavity comprising:
   providing a device comprising an elongated structural member adapted for engagement with a conventional syringe, a cannula assembly capable of engagement with the syringe, a saddle in which the syringe is seated and which permits conduit with the cannula assembly, and a mechanism in communication with the elongated structural member for advancing the surgical material through the cannula assembly;
   loading the surgical material into the syringe;
   engaging the syringe with the cannula assembly and seating the syringe in the saddle of the device;
   inserting the cannula portion of the device into the body cavity;
   positioning the distal tip of the cannula within proximity of the target site;
   applying the surgical material having a viscosity greater than 50,000 centipoise directly to the target site; and
   withdrawing the apparatus from the body cavity.

23. The method of claim 22 wherein applying the surgical material to the target site comprises application against gravity.

24. The method of claim 22 further comprising priming of the syringe and or cannula assembly.

25. The method of claim 22 wherein the mechanism for advancing the surgical material through the cannula assembly is a drive mechanism.

26. The method of claim 22 wherein the mechanism for advancing the surgical material through the cannula assembly comprises a spring-reinforced assembly.

27. The method of claim 22 wherein applying the surgical material to the target site comprises replacing a spent syringe with a syringe containing an additional volume of surgical material.

28. The method of claim 22 wherein the device further comprises application of the surgical material to the target site through a flexible and generally fan shaped applicator tip which is attached to the cannula assembly at its distal end.

29. A method of delivering a surgical material to a target site within a body cavity comprising:

providing a device comprising an elongated structural member adapted for engagement with a conventional syringe, a cannula assembly capable of engagement with the syringe, a saddle in which the syringe is seated and which permits conduit with the cannula assembly; a drive mechanism in communication with the elongated structural member for advancing the surgical material through the cannula assembly, an applicator tip attached to a distal end of the cannula assembly and a secondary mechanism which permits air bolus priming of the syringe and which disengages the elongated structural member upon actuation;

loading the surgical material into the syringe;

connecting the syringe to the cannula assembly and seating the syringe in the saddle of the device;

inserting the cannula portion of the device into the body cavity;

positioning the distal tip of the cannula within proximity of the target site;

applying the surgical material to the target site wherein the surgical material has a viscosity greater than about 50,000 centipoise;

optionally replacing the syringe with the same or another syringe containing an additional volume of surgical material; and withdrawing the apparatus from the body cavity.

30. A method of reducing adhesions between bodily tissues at a target anatomical site within a body cavity comprising:

providing a device comprising an elongated structural member adapted for engagement with a conventional syringe, a cannula assembly capable of engagement with the syringe, a surface on which the syringe is seated and which permits flow communication of the surgical material through the cannula assembly; a mechanism in communication with the elongated structural member for advancing an adhesion barrier material through the cannula assembly, a flexible applicator tip attached to a distal end of the cannula assembly for advancing an adhesion barrier material there through and a secondary mechanism which permits priming of the syringe and which disengages the elongated structural member upon actuation;

loading the syringe with the adhesion barrier material;

connecting the syringe to the cannula assembly and seating the syringe in the device;

inserting the cannula portion of the device into the body cavity;

locating the distal tip of the cannula within proximity of the target anatomical site;

applying the adhesion barrier material to the target anatomical site; and withdrawing the apparatus from the body cavity.

31. The method of claim 30 wherein applying the adhesion barrier material to the target anatomical site comprises replacing a spent syringe with a syringe containing an additional volume of adhesion barrier material.

32. The method of claim 30 wherein the distal tip of the cannula is formed to include a fan-shaped member and the fan-shaped member is positioned in the target anatomical site to apply the adhesion barrier material to cardiac tissue.

33. The method of claim 30 wherein the distal tip of the cannula is formed to include a fan-shaped member and the fan-shaped member is positioned in the target anatomical site to apply the adhesion barrier material to abdominal tissue.

34. A method for sealing a bodily organ or tissue at a target anatomical site within a body cavity comprising:

providing a device comprising an elongated structural member adapted for engagement with a conventional syringe, a cannula assembly capable of engagement with the syringe, a surface on which the syringe is seated and which permits flow communication of the surgical material through the cannula assembly; a mechanism in communication with the elongated structural member for advancing an anatomical filler material through the cannula assembly, an applicator tip attached to a distal end of the cannula assembly and a secondary mechanism which permits priming of the syringe and which disengages the elongated structural member upon actuation;

loading the syringe with the anatomical filler material;

connecting the syringe to the cannula assembly and seating the syringe in the device;

inserting the cannula portion of the device into the body cavity;

locating the distal tip of the cannula within proximity of the target anatomical site;

applying the anatomical filler material to the target anatomical site wherein the anatomical filler material has a viscosity greater that 50,000 centipoise; and withdrawing the apparatus from the body cavity.

35. The method of claim 34 wherein applying the anatomical filler material to the target anatomical site comprises replacing a spent syringe with a syringe containing an additional volume of anatomical filler material.

36. The method of claim 34 wherein the distal tip of the cannula is formed to include a fan-shaped member and the fan-shaped member is a flexible member that is positioned in the target anatomical site to apply the anatomical filler material to cardiac tissue.

37. The method of claim 34 wherein the distal tip of the cannula is formed to include a fan-shaped member and the fan-shaped member is a flexible member that is positioned in the target anatomical site to apply the anatomical filler material to abdominal tissue.

* * * * *